US011714089B2

(12) United States Patent
Arber et al.

(10) Patent No.: US 11,714,089 B2
(45) Date of Patent: Aug. 1, 2023

(54) COMBINATION OF MARKERS FOR DIAGNOSING CANCER (71) Applicant: The Medical Research, Infrastructure and Health Services Fund of the Tel Aviv Medical Center, Tel-Aviv (IL)

(72) Inventors: Nadir Arber, Tel-Aviv (IL); Shiran Shapira, Petach-Tikva (IL); Diana Kazanov, Rishon-LeZion (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 276 days.

(21) Appl. No.: 16/615,423

(22) PCT Filed: May 21, 2018

(86) PCT No.: PCT/IL2018/050550
§ 371 (c)(1),
(2) Date: Nov. 21, 2019

(87) PCT Pub. No.: WO2018/216006
PCT Pub. Date: Nov. 29, 2018

(65) Prior Publication Data
US 2020/0174004 A1 Jun. 4, 2020

Related U.S. Application Data (60) Provisional application No. 62/509,118, filed on May 21, 2017.

(51) Int. Cl.
*G01N 33/574* (2006.01)
*A61K 45/06* (2006.01)

(52) U.S. Cl.
CPC ........ *G01N 33/57492* (2013.01); *A61K 45/06* (2013.01)

(58) Field of Classification Search
CPC ... G01N 33/57492; G01N 2333/70546; G01N 2800/52; G01N 2800/50; G01N 2333/70596; G01N 33/57419; G01N 33/57438; G01N 33/57426; G01N 33/574; A61K 45/06; C07K 14/70596; A61P 35/00
See application file for complete search history.

(56) References Cited

U.S. PATENT DOCUMENTS

2004/0005596 A1   1/2004  Li et al.
2010/0273191 A1*  10/2010 Arber ............... G01N 33/57419
                                                   435/7.23

FOREIGN PATENT DOCUMENTS

WO   WO 2005/114191   12/2005
WO   WO 2007/088537    8/2007
WO   WO 2009/074988    6/2009
WO   WO 2018/216006   11/2019

OTHER PUBLICATIONS

Kraus et al.Predictive Levels of CD24 in Peripheral Blood Leukocytes for the Early Detection of Colorectal Adenomas and Adenocarcinomas. Disease Markers 2015: 1-9, published online May 11, 2015.*
Miltenyi Biotec. (Blood, 7 pages, 2021).*
Shapira et al., Feasibly of CD24/CD11b as a screening test for hematological malignancies. J. Pers. Med 11 (724): 1-9, 2021.*
Yu et al. (PLOS One 1-23 and Supplemental Table 2, Mar. 3, 2016).*
International Preliminary Report on Patentability dated Dec. 5, 2019 From the International Bureau of WIPO Re. Application No. PCT/IL2018/050550. (9 Pages).
International Search Report and the Written Opinion dated Aug. 21, 2018 From the International Searching Authority Re. Application No. PCT/TL2018/050550. (12 Pages).
Kraus et al. "Predictive Levels of CD24 in Peripheral Blood Leukocytes for the Early Detection of Colorectal Adenomas and Adenocarcinomas", Disease Markers, 2015(Art.ID916098): 1-9, Published Online May 11, 2015. Abstract, Table 2, p. 7, 1-h Col., 2nd Para.
Sagiv et al. "CD24 Is A New Oncogene, Early at the Multistep Process of Colorectal Cancer Carcinogenesis", Gastroenterology, 131(2): 630-639, Aug. 2006.
Sagiv et al. "Gene Expression Analysis Proposes Alternative Pathways for the Mechanism by Which Celecoxib Selectively Inhibits the Growth of Transformed But Not Normal Enterocytes", Clinical Cancer Research, 13(22): 6807-6815, Nov. 15, 2007.
Sagiv et al. "Gene Expression Following Exposure to Celecoxib in Humans: Pathways of Inflammation and Carcinogenesis Are Activated in Tumors But Not Normal Tissues", Digestion, 84(3): 169-184, Published Online May 5, 2011.
Shapira et al. "An Immunoconjugate of Anti-CD24 and Pseudomonas Exotoxin Selectively Kills Human Colorectal Tumors in Mice", Gastroenterology, 140(3): 935-946, Published Online Dec. 11, 2010.
Toth et al. "Detection of Methylated SEPT9 in Plasma Is A Reliable Screening Method for Both Left- and Right-Sided Colon Cancers", PLOS One, 7(9): e46000-1-e46000-7, Sep. 25, 2012.
Warren et al. "Septin 9 Methylated DNA Is A Sensitive and Specific Blood Test for Colorectal Cancer", BMC Medicine, 9: 133-1-133-9, Dec. 14, 2011.
Supplementary European Search Report and the European Search Opinion dated May 4, 2021 From the European Patent Office Re. Application No. 18806819.1. (10 Pages).

(Continued)

*Primary Examiner* — Alana Harris Dent (57) ABSTRACT

A method of diagnosing a cancer or a pre-malignant lesion is disclosed. The method comprising determining a level of expression of CD24 on leukocytes comprised in a biological sample of a subject, wherein a level of CD24 on small leukocytes and not on large leukocytes above a predetermined threshold is indicative of the cancer or the pre-malignant lesion. A method of monitoring efficacy of cancer therapy and a kit for diagnosing a cancer or a pre-malignant lesion are also disclosed.

11 Claims, 6 Drawing Sheets

(56) References Cited

OTHER PUBLICATIONS

Kraus et al. "S1119CD24 is a Novel Blood Biomarker for the Early Oetection of Colorectal Adenomas and Adenocarcinomas", Gastroenterology, 138(5); 184, May 1, 2010.
Kraus et al. "S1128, Identification of CD24, a Novel Biomarker for the Early Oetection of Colorectal Cancer (CRC), U sing Peripheral Blood Mononuclear Cells", S1128, Gastroenterology, 134(4):P.A-184, Apr. 1, 2008.
Miller et al. "Increased Expression of CD24 in Nonmelanoma Skin Cancer", The International Journal of Biological Makers, 27(4): e331-e336, Published at OOTR Annual Conference Proceedings 2012.
Communication Pursuant to Article 94(3) EPC dated Jan. 31, 2022 From the European Patent Office Re. Application No. 18806819.1. (6 Pages).

\* cited by examiner

COMBINATION OF MARKERS FOR DIAGNOSING CANCER

RELATED APPLICATIONS

This application is a National Phase of PCT Patent Application No. PCT/IL2018/050550 having International filing date of May 21, 2018, which claims the benefit of priority under 35 USC § 119(e) of U.S. Provisional Patent Application No. 62/509,118 filed on May 21, 2017. The contents of the above applications are all incorporated by reference as if fully set forth herein in their entirety.

FIELD AND BACKGROUND OF THE INVENTION

The present invention, in some embodiments thereof, relates to methods for diagnosing cancer or pre-disposition thereto by determining the expression level of $CD24^+$ $CD11b^-$ in a sample comprising leukocytes.

CD24, a mucin-like cell surface molecule, is highly expressed in large variety of solid tumors as well as in hematological malignancies, already early in the multistep process of carcinogenesis, and was found to be correlated with poor prognosis and a more aggressive course of the disease. Conjugation of anti-CD24 (SWA11) monoclonal antibodies (mAbs) to a *Pseudomonas* exotoxin truncated derivative (PE38) was previously shown to selectively kill human cancer cells in mice and induce apoptosis without toxicity to normal tissues [Shapira et al., Gastroenterology (2011) 140: 935-946]. Novel humanized monoclonal antibodies directed towards CD24 were developed at the ICPC (Integrated Cancer Prevention Center) and found to be specific for CD24-expressing cancer cells.

Colorectal cancer (CRC) is a major health concern worldwide (1.2 million new cases per year and about half a million deaths worldwide). CRC carcinogenesis is a multi-step process spanning over 10-20 years, which provides a window of opportunity for effective intervention and prevention. Removing the pre-malignant lesion, the adenoma, can prevent CRC. Early detection, e.g. when the patient is asymptomatic, is the single most important therapy. Early detection can significantly improve morbidity and mortality. However, although these strategies are considered standard clinical practice, their impact is limited due to invasiveness, low adherence, or high cost. The number of deaths due to CRC remains alarmingly high, and makes CRC prevention paramount.

Pancreatic cancer (PC) is the fourth leading cause of cancer deaths, being responsible for 7% of all cancer-related deaths in both men and women. There is no standard diagnostic tool for PC. When diagnosed early, surgical resection offers the best chance for long term survival for this devastating cancer, which currently has less than 5% five year survival and a mean life expectancy of 3-6 months.

Lymphomas and Leukemia are highly heterogeneous diseases, varying by both the type of the malignant cell and the tumor location. There is currently no blood test or other screening tool for early detection and diagnosis.

Early diagnosis has been shown to significantly improve prognosis and to significantly decrease morbidity and mortality of various types of cancers. The screening tool must be sufficiently non-invasive, inexpensive and allow widespread applicability so that healthy populations would be willing to do it periodically. Thus, for example, a simple blood test increases screening compliance, promoting early detection and better patient outcomes. Such an example is the blood-based Septin 9 (SEPT9) methylated DNA test which specifically detects CRCs with an overall sensitivity of 90% [Kristiansen G et al., *J Mol Histol* (2004) 35:255-62; Warren J D et al., *BMC Med* (2011) vol. 9: article 133]. However, the plasma Septin 9 test detected only 12% of adenomas with a false-positive rate of 3% and the stool test was later shown to be more accurate [Tóth K et al., *PLoS One* (2012) vol. 7(9): Article ID e46000].

Some inventors of the present invention have previously developed a technology for detection and diagnosis of various human malignancies. For example, it was previously shown that expression level of CD24 in peripheral blood leukocytes may be used for the early detection of colorectal adenomas and CRC [Kraus et al., *Dis Markers* (2009) doi: 10.1155/2015/916098. Epub 2015 May 11].

Additional background art include:

U.S. Patent Application no. 20040005596 to Li J. et al. discloses methods of diagnosing cancer by determining the level of CD24 in situ in tissue samples suspected to be precancerous or cancerous.

PCT Publication No. WO 2007/088537 to Arber N. discloses methods of diagnosing cancer by determining the level of circulating, non-anchored CD24 in a biological sample of a subject (e.g. in a stool sample, a serum sample, a blood sample, a urine sample, or a saliva sample).

PCT Publication No. WO 2009/074988 to Arber N. discloses method of diagnosing cancer or a pre-malignant lesion. The method comprises determining a level of CD24 expressed on peripheral blood cells of a subject in need thereof, wherein the level of CD24 above a predetermined threshold is indicative of the cancer or the pre-malignant lesion.

SUMMARY OF THE INVENTION

According to an aspect of some embodiments of the present invention there is provided a method of diagnosing a cancer or a pre-malignant lesion, the method comprising determining a level of expression of CD24 on leukocytes comprised in a biological sample of the subject, wherein a level of CD24 on small leukocytes and not on large leukocytes above a predetermined threshold is indicative of the cancer or the pre-malignant lesion.

According to an aspect of some embodiments of the present invention there is provided a method treating a cancer or a pre-malignant lesion in a subject in need thereof, the method comprising: (a) diagnosing the subject according to the method of some embodiments of the invention; and (b) administering a therapeutic agent for the treatment of the cancer or the pre-malignant lesion to the diagnosed subject, thereby treating cancer or a pre-malignant lesion in the subject in need thereof.

According to an aspect of some embodiments of the present invention there is provided a method of monitoring efficacy of cancer therapy, the method comprising determining a level of expression of CD24 on leukocytes comprised in a biological sample of the subject having been treated with a cancer therapy, wherein a decrease in a level of CD24 on small leukocytes and not on large leukocytes from a predetermined threshold following the cancer therapy is indicative of reduction of the cancer, thereby monitoring efficacy of the cancer therapy.

According to an aspect of some embodiments of the present invention there is provided a kit for diagnosing a cancer or a pre-malignant lesion, comprising a packaging material and at least one agent for determining a level of CD24 expression and at least one agent for determining a level of CD11b expression.

According to an aspect of some embodiments of the present invention there is provided a composition comprising at least 70% small leukocytes and a CD24 targeting antibody.

According to some embodiments of the invention, the method further comprises determining a level of expression of CD11b on the leukocytes.

According to some embodiments of the invention, the small leukocytes have a CD24$^+$CD11b$^-$ signature.

According to some embodiments of the invention, the small leukocytes are selected from the group consisting of T lymphocytes, B lymphocytes and monocytes.

According to some embodiments of the invention, the large leukocytes have a CD24$^+$CD11b$^-$ signature.

According to some embodiments of the invention, the large leukocytes are selected from the group consisting of neutrophils, dendritic cells, granulocytes, macrophages and NK cells.

According to some embodiments of the invention, the method further comprises corroborating the diagnosis using a diagnostic assay selected from a biopsy, a histology, a CT scan (Computed Tomography) and an MRI (Magnetic Resonance Imaging).

According to some embodiments of the invention, the sample is selected from the group consisting of a blood sample, a serum sample, a stool sample, a urine sample and a saliva sample According to some embodiments of the invention, the determining is effected ex vivo.

According to some embodiments of the invention, the determining is effected at the protein level.

According to some embodiments of the invention, the determining is effected by flow cytometry.

According to some embodiments of the invention, the determining is effected at the polynucleotide level.

According to some embodiments of the invention, the method further comprises administering to the subject a therapeutic agent for the treatment of the cancer or the pre-malignant lesion.

According to some embodiments of the invention, the therapeutic agent is selected from the group consisting of a chemotherapeutic agent, an antibody immunotherapy, a radiation therapy, a cancer vaccine, an anti-inflammatory agent and a dietary supplement.

According to some embodiments of the invention, the at least one agent comprises a polypeptide agent.

According to some embodiments of the invention, the polypeptide agent comprises an antibody.

According to some embodiments of the invention, the antibody is attached to a detectable moiety.

According to some embodiments of the invention, the at least one agent comprises an oligonucleotide agent.

According to some embodiments of the invention, the pre-malignant lesion is an adenoma.

According to some embodiments of the invention, the pre-malignant lesion is associated with a solid tumor.

According to some embodiments of the invention, the cancer is a solid tumor.

According to some embodiments of the invention, the solid tumor is a gastrointestinal tract cancer.

According to some embodiments of the invention, the solid tumor is selected from the group consisting of colorectal cancer, cancer of the small intestine, stomach cancer, pancreatic cancer, liver cancer, gall-bladder cancer, biliary tract cancer, esophageal cancer, oral cavity cancer, prostate cancer, testicular cancer, lung cancer, breast cancer, urinary tract cancer, kidney cancer, bladder cancer, uterine cancer, cervical cancer, ovarian cancer, fallopian tube cancer, sarcoma, melanoma, squamous cell carcinoma, brain cancer and glioma.

According to some embodiments of the invention, the cancer is a hematopoietic malignancy.

According to some embodiments of the invention, the hematopoietic malignancy is selected from the group consisting of a lymphoma, a leukemia and a multiple myeloma.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-D are graphs illustrating the Empirical ROC curves.

DESCRIPTION OF SPECIFIC EMBODIMENTS OF THE INVENTION

The present invention, in some embodiments thereof, relates to methods for diagnosing cancer or pre-disposition thereto by determining the expression level of $CD24^+$ $CD11b^-$ in a sample comprising leukocytes.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CD24 is highly expressed in numerous malignant tissues among them B-cell lymphomas, gliomas, prostate, gastric, pancreatic and non-small cell lung carcinomas. Increased expression of CD24 is usually tied with a more aggressive course of the disease.

Early diagnosis has been shown to significantly improve prognosis and to significantly decrease morbidity and mortality of various types of cancers. Previous work disclosed methods of diagnosing cancer by determining the level of circulating, non-anchored CD24 in a biological sample of a subject (e.g. in a stool sample, a serum sample, a blood sample, a urine sample, or a saliva sample) or methods of diagnosing cancer or a pre-malignant lesion by determining a level of CD24 expressed on peripheral blood cells of a subject.

While reducing the present invention to practice, the present inventors have uncovered an improved and simple screening assay for cancer diagnosis by detecting CD24 expression on small leukocytes. Thus, according to the present teachings, elevated levels of $CD24^+CD11b^-$ leukocytes are associated with cancer, pre-malignant lesion or predisposition thereto.

To characterize the expression profiling of CD24 and CD11b, peripheral blood leukocytes (PBLs) from cancer patients and age and gender matched healthy individuals were separated from freshly drawn blood and the dual expression of CD24 and CD11b was analyzed using flow cytometry. The present inventors further generated a template file for analysis of the samples using gates within the software to create a hierarchical population tree at the beginning of the screen. This template file is used to analyze the samples after data acquisition is complete. The template file includes compensation adjustment, which is uniformly applied to all the data collected in order to minimize fluorescence overlap between detection channels.

Using this template file, the results confirmed that cancer subjects had elevated levels of $CD24^+CD11b^-$ leukocytes as compared to healthy (i.e. normal) subjects. The healthy subjects were further verified for being in good health using thorough and extensive examination at the Integrated Cancer Prevention Center at the Tel Aviv Medical Center (as previously discussed in Sella T. et al., *Eur J Intern Med* (2013) 24(3): 245-9). Cancer was verified by histology in all patients.

Taken together, this simple, non-invasive test can be used to reliably identify individuals with various pre-cancers and cancers (such as colorectal adenomas, early carcinoma, pancreatic and other solid and hematological tumors) or predisposition thereto.

Thus, according to one aspect of the present invention, there is provided a method of diagnosing a cancer or a pre-malignant lesion, the method comprising determining a level of expression of CD24 on leukocytes comprised in a biological sample of a subject, wherein a level of CD24 on small leukocytes and not on large leukocytes above a predetermined threshold is indicative of the cancer or the pre-malignant lesion.

As used herein, the term "diagnosing" refers to classifying a pathology (e.g., a CD24-associated cancer or a pre-malignant lesion) or a symptom, determining a severity of the pathology, monitoring pathology progression, forecasting an outcome of a pathology and/or prospects of recovery.

As used herein, the phrase "pre-malignant lesion" refers to a mass of cells and/or tissue having increased probability of transforming into a malignant tumor. According to one embodiment, in the pre-malignant lesion of the present invention CD24 is over-expressed on small leukocytes as compared to a non-malignant tissue or cell. Examples of CD24-associated pre-malignant lesions include, but are not limited to, adenomatous polyps, Barrett's esophagus, IPMN (Intraductal Papillary Mucinus Neoplasia), DCIS (Ductal Carcinoma in Situ) in the breast, leukoplakia and erythroplakia.

According to a specific embodiment, the pre-malignant lesion is an adenoma.

According to a specific embodiment, the pre-malignant lesion is associated with a solid tumor.

According to a specific embodiment, the pre-malignant lesion is associated with a non-solid tumor.

Thus, the pre-malignant lesion which is diagnosed according to the method of this aspect of the present invention can transform into a malignant solid or non-solid (e.g., hematological malignancies) cancer (or tumor). According to a specific embodiment, the pre-malignant lesion which is diagnosed by the method of this aspect of the present invention is an adenomatous polyp of the colon, an adenomatous polyp of the rectum, an adenomatous polyp of the small bowel and Barrett's esophagus.

Non-limiting examples of cancers which can be diagnosed by the method of this aspect of the present invention (i.e. by analysis of over-expression of CD24 on small leukocytes) include tumors of the gastrointestinal tract (colon cancer, rectum cancer, anal region cancer, colorectal cancer, small and/or large bowel cancer, esophageal cancer, stomach cancer, pancreatic cancer, gastric cancer, small intestine cancer, adenocarcinoma arising in the small intestine, carcinoid tumors arising in the small intestine, lymphoma arising in the small intestine, mesenchymal tumors arising in the small intestine, gastrointestinal stromal tumors), gallbladder carcinoma, Biliary tract tumors, prostate cancer, kidney (renal) cancer (e.g., Wilms' tumor), liver cancer (e.g., hepatoblastoma, hepatocellular carcinoma), hepatobiliary cancer, biliary tree cancer, tumors of the Gallbladder, bladder cancer, embryonal rhabdomyosarcoma, germ cell tumor, trophoblastic tumor, testicular germ cells tumor, immature teratoma of ovary, uterine, epithelial ovarian cancer, sacrococcygeal tumor, choriocarcinoma, placental site trophoblastic tumor, epithelial adult tumor, ovarian cancer, cervical cancer, cancer of the vagina, cancer of the Vulva, lung cancer (e.g., small-cell and non-small cell lung carcinoma), nasopharyngeal, breast cancer, squamous cell carcinoma (e.g., in head and neck), oral cavity cancer, neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic, cutaneous T-cell lymphoma, primary central nervous system lymphoma), gliomas, medullary thyroid carcinoma, testicular cancer, brain and head/neck cancer, gynecologic cancer, endometrial cancer, germ cell tumors, mesenchymal tumors, neurogenic tumors, cancer of the bladder, cancer of the ureter, cancer of the renal pelvis, cancer of the urethra, cancer of the penis, cancer of the testis, cancers of the uterine body, endometrial carcinoma, uterine sarcoma, peritoneal carcinoma and Fallopian Tube carcinoma, germ cell tumors of the ovary, sex cord-stromal tumors, cancer of the endocrine system, thyroid tumors, medullary thyroid carcinoma, thyroid lymphoma, parathyroid tumors, adrenal tumors, pancreatic endocrine tumors, sarcomas of the soft tissue and bone, benign and malignant mesothelioma, malignant peritoneal mesothelioma, malignant mesothelioma of the Tunica Vaginalis Testis, malignant mesothelioma of the Pericardium, skin cancer, cutaneous melanoma, intraocular melanoma, neoplasms of the central nervous system, medulloblastomas, meningiomas, peripheral nerve tumors, Pineal region tumors, pituitary adenomas, craniopharyngiomas, acoustic neuromas, Glomus Jugulare tumors, Chordomas and Chondrosarcomas, Hemangioblastomas, Choroid Plexus Papillomas and Carcinomas, spinal axis tumors, leukemia, acute leukemia, chronic leukemia and a multiple myeloma.

According to some embodiments of the invention, the cancer is a solid tumor.

According to some embodiments of the invention, the solid tumor is a gastrointestinal tract cancer.

According to some embodiments of the invention, the solid tumor is selected from the group consisting of colorectal cancer, cancer of the small intestine, stomach cancer, pancreatic cancer, liver cancer, gall-bladder cancer, biliary tract cancer, esophageal cancer, oral cavity cancer, prostate cancer, testicular cancer, lung cancer (e.g. non-small cell lung carcinoma), breast cancer, urinary tract cancer, kidney cancer, bladder cancer, uterine cancer, cervical cancer, ovarian cancer, fallopian tube cancer, sarcoma, melanoma, squamous cell carcinoma, brain cancer and glioma.

According to some embodiments of the invention, the cancer is a non-solid tumor (e.g. hematopoietic malignancy).

According to some embodiments of the invention, the hematopoietic malignancy is a lymphoma, leukemia or multiple myeloma.

According to a specific embodiment, the hematopoietic malignancy is a Hodgkin lymphoma, a non-Hodgkin lymphoma, a chronic leukemia (e.g. chronic lymphocytic leukemia (CLL)), an acute leukemia (e.g. acute lymphocytic leukemia (ALL)), a B cell leukemia, a B cell lymphoma, a Burkitt leukemia, a cutaneous T cell lymphoma (CTCL), histiocytic, lymphoblastic, T cell, thymic, etc.).

As used herein the phrase "subject in need thereof" or "subject" refers to an animal, preferably a mammal, most preferably a human being, at any age or gender who is at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject can be a healthy human subject undergoing a routine well-being check-up.

As used herein the term "CD24" refers to the nucleic acid sequence and/or the amino acid sequence of at least a functional portion of the phosphatidylinositol-anchored mucin-like cell-surface protein. An exemplary CD24 protein is provided in GenBank Accession No. NP_037362.1. An exemplary CD24 transcript is provided in GenBank Accession No. NM_013230.2.

As used herein, the phrase "level of expression of CD24" refers to the degree of gene expression and/or gene product activity of CD24 in the biological sample. Accordingly, the level of CD24 can be determined at the amino acid level using protein detection methods or at the nucleic acid level using RNA detection methods (as discussed in further detail herein below).

As used herein the term "CD11b" refers to the nucleic acid sequence and/or the amino acid sequence of at least a functional portion of the Integrin alpha M (ITGAM) cell-surface protein. Exemplary CD11b proteins are provided in GenBank Accession Nos. NP_000623.2 and NP_001139280.1. Exemplary CD11b transcripts are provided in GenBank Accession Nos. NM_000632 and NM_001145808.

As used herein, the phrase "level of expression of CD11b" refers to the degree of gene expression and/or gene product activity of CD11b in the biological sample. Accordingly, the level of CD11b can be determined at the amino acid level using protein detection methods or at the nucleic acid level using RNA detection methods (as discussed in further detail herein below).

As used herein the term "leukocytes" refers to white blood cells. Exemplary leukocytes include, but are not limited to, T lymphocytes (also known as T cells), B lymphocytes (also known as B cells), monocytes, macrophages, granulocytes, neutrophils, dendritic cells and NK cells.

The term "small leukocytes" refers to lymphocytes ranging in size between 6 and 9 μm in diameter. These typically include T lymphocytes (also known as T cells), B lymphocytes (also known as B cells) and monocytes. According to a specific embodiment, small leukocytes typically comprise a $CD24^+CD11b^-$ signature.

According to one embodiment small leukocytes may express the following markers: CD24, CD3, CD4, CD8, CD19, CD20, CD14, CD16 and/or CD33.

According to one embodiment, small leukocytes lack expression of CD11b, i.e. are $CD11b^-$.

According to a specific embodiment small leukocytes express a $CD24^+CD3^+CD4^+$ signature (e.g. T cells).

According to a specific embodiment small leukocytes express a $CD24^+CD3^+CD8^+$ signature (e.g. T cells).

Accordingly, according to one embodiment, T cells are identified using an antibody which specifically binds to CD24, CD3, CD4 and/or CD8.

According to a specific embodiment small leukocytes express a $CD24^+CD19^+$ signature (e.g. B cells).

According to a specific embodiment small leukocytes express a $CD24^+CD20^+$ signature (e.g. B cells).

Accordingly, according to one embodiment, B cells are identified using an antibody which specifically binds to CD24, CD19 and/or CD20.

According to a specific embodiment small leukocytes express a $CD24^+CD14^+$ signature (e.g monocytes).

According to a specific embodiment small leukocytes express a $CD24^+CD16^+$ signature (e.g. monocytes).

According to a specific embodiment small leukocytes express a $CD24^+CD33^+$ signature (e.g. monocytes).

Accordingly, according to one embodiment, monocytes are identified using an antibody which specifically binds to CD24, CD14, CD16 and/or CD33.

According to one embodiment, small leukocytes comprise a heterogeneous population of cells, i.e. comprising more than one cell type, e.g. T cells, B cells and/or monocytes, such as e.g. CD24$^+$CD3$^+$CD4$^+$/CD8$^+$ T cells, CD24$^+$CD19$^+$/CD20$^+$ B cells, and/or CD24$^+$CD14$^+$/CD16$^+$/CD33$^+$ monocytes).

The term "large leukocytes" refers to lymphocytes ranging in size above 9 μm in diameter and which contain more cytoplasm and scattered granules (as compared to small leukocytes). These typically include granulocytes (e.g. neutrophils and eosinophils), dendritic cells, macrophages and NK cells. According to a specific embodiment, large leukocytes comprise a CD24$^+$CD11b$^-$ signature.

According to one embodiment large leukocytes may express the following markers: CD11b, CD66b, CD11c, CD123, CD56 and/or CD68.

According to a specific embodiment large leukocytes express a CD66b marker (e.g. granulocytes). Accordingly, according to one embodiment, granulocytes are identified using an antibody which specifically binds to CD66b.

According to a specific embodiment large leukocytes express a CD11c and/or CD123 marker (e.g. dendritic cells). Accordingly, according to one embodiment, dendritic cells are identified using an antibody which specifically binds to CD11c and/or CD123.

According to a specific embodiment large leukocytes express a CD56 marker (e.g. NK cells). Accordingly, according to one embodiment, NK cells are identified using an antibody which specifically binds to CD56.

According to a specific embodiment large leukocytes express a CD68 marker (e.g. macrophages). Accordingly, according to one embodiment, NK cells are identified using an antibody which specifically binds to CD68.

According to one embodiment, large leukocytes comprise a heterogeneous population of cells, i.e. comprising more than one cell type, e.g. macrophages, NK cells, dendritic cells and granulocytes.

According to one embodiment, the CD24 is anchored to leukocytes (i.e. it does not refer to free, non-anchored CD24).

According to one embodiment, the CD11b is anchored to leukocytes (i.e. it does not refer to free, non-anchored CD11b).

The phrase "biological sample" as used herein refers to any sample which comprises leukocytes. Examples include but are not limited to, a blood sample (e.g., serum), a saliva sample, a stool sample, a urine sample, a pup smear, a cervix sample, a bone marrow sample, a lymph fluid, an ascites fluid, a skin sample, various external secretions of the respiratory, intestinal, and genitourinary tracts, tears, milk, a tissue biopsy sample, a cerebrospinal fluid (CSF) sample, a sperm fluid sample, amniotic fluid sample, and chorionic villi sample (CVS), and also samples of in vivo cell culture constituents. It should be noted that a "biological sample of a subject" may also optionally comprise a sample that has not been physically removed from the subject.

According to one embodiment, the biological sample contains small leukocytes.

According to one embodiment, the biological sample contains large leukocytes.

According to one embodiment, the biological sample does not contain large leukocytes.

According to one embodiment, the biological sample containing leukocytes is a blood sample (e.g. peripheral blood sample).

According to one embodiment, the biological sample containing leukocytes is a peripheral blood lymphocyte (PBL) sample.

According to one embodiment, the biological sample containing leukocytes is a biopsy sample (e.g. a cancer or pre-malignant biopsy sample).

Numerous well known tissue or fluid collection methods can be utilized to collect the biological sample or the cells (e.g. leukocytes) from the subject in order to determine the level of CD24 and CD11b expression (or any of the other cell markers described above). Examples include, but are not limited to, syringe with a needle, fine needle biopsy, needle biopsy, core needle biopsy and surgical biopsy, buccal smear and lavage. Regardless of the procedure employed, once a biological sample is obtained the level of the variant can be determined and a diagnosis can thus be made.

Methods of processing biological samples so as to obtain leukocytes therefrom are well known in the art and include, for example, lysis of erythrocytes, isolation of mononuclear cells by density gradient separation, and assorted non-flow sorting methods, such as magnetic bead separations (for enrichment of specific cell populations e.g. monocytes, T lymphocytes, B lymphocytes). The biological sample may also be processed to obtain small or large leukocytes based on size using any method known in the art, such as by filtration.

It will be appreciated that determining the level of CD24 and/or CD11b in leukocytes can be effected ex vivo (on a sample derived from the subject) as well as in vivo (within the subject). Likewise, the expression level of any one of CD3, CD4, CD8, CD19, CD20, CD14, CD16 and/or CD33 on small leukocytes or CD66b, CD11c, CD123, CD56 and/or CD68 on large leukocytes can be effected ex vivo or in vivo.

According to one embodiment, the level of the CD24 and/or CD11b amino acid sequence (CD24 and/or CD11b protein) is determined using a CD24 and/or CD11b specific antibody, respectively, via the formation of an immunocomplex [i.e., a complex formed between the CD24 and/or CD11b antigen (a CD24 and/or CD11b amino acid sequence) present in the biological sample and the CD24 and/or CD11b specific antibody, respectively].

According to one embodiment, the level of the CD3, CD4, CD8, CD19, CD20, CD14, CD16, CD33, CD66b, CD11c, CD123, CD56 and/or CD68 amino acid sequence (CD3, CD4, CD8, CD19, CD20, CD14, CD16, CD33, CD66b, CD11c, CD123, CD56 and/or CD68 proteins, respectively) is determined using specific antibodies via the formation of an immunocomplex [i.e., a complex formed between the antigen present in the biological sample and the specific antibody].

The immunocomplex of the present invention can be formed at a variety of temperatures, salt concentration and pH values which may vary depending on the method and the biological sample used and those of skills in the art are capable of adjusting the conditions suitable for the formation of each immunocomplex.

The term "antibody" as used in this invention includes intact molecules as well as functional fragments thereof, such as Fab, F(ab')2, Fv or single domain molecules such as VH and VL to an epitope of an antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to the method of this aspect of the present invention, an amount of immunocomplex formation is indicative of a diagnosis of the cancer or the pre-malignant lesion. Various methods can be used to detect the formation of the immunocomplex of the present invention (e.g. CD24 and/or CD11b immunocomplex) of the present invention and those of skills in the art are capable of determining which method is suitable for each immunocomplex.

The antibody (e.g. CD24 and/or CD11b antibody) used in the immunocomplex of the present invention can be labeled using methods known in the art. It will be appreciated that the labeled antibodies can be either primary antibodies (i.e., which bind to the specific antigen, e.g., a CD24 antigen and/or CD11b antigen) or secondary antibodies (e.g., labeled goat anti rabbit antibodies, labeled mouse anti-human antibody) which bind to the primary antibodies. The antibody can be directly conjugated to a label or can be conjugated to an enzyme.

Antibodies of the present invention can be fluorescently labeled (using a fluorescent dye conjugated to an antibody), radiolabeled (using radiolabeled e.g., $^{125}$I, antibodies), or conjugated to an enzyme (e.g., horseradish peroxidase or alkaline phosphatase) and used along with a chromogenic substrate to produce a colorimetric reaction. The chromogenic substrates utilized by the enzyme-conjugated antibodies of the present invention include, but are not limited to, AEC, Fast red, ELF-97 substrate [2-(5'-chloro-2-phosphoryloxyphenyl)-6-chloro-4(3H)-quinazolinone], p-nitrophenyl phosphate (PNPP), phenolphthalein diphosphate, and ELF 39-phosphate, BCIP/INT, Vector Red (VR), salmon and magenta phosphate (Avivi C., et al., 1994, J Histochem. Cytochem. 1994; 42: 551-4) for alkaline phosphatase enzyme and Nova Red, diaminobenzidine (DAB), Vector(R) SG substrate, luminol-based chemiluminescent substrate for the peroxidase enzyme. These enzymatic substrates are commercially available from Sigma (St Louis, Mo., USA), Molecular Probes Inc. (Eugene, Oreg., USA), Vector Laboratories Inc. (Burlingame, Calif., USA), Zymed Laboratories Inc. (San Francisco, Calif., USA), Dako Cytomation (Denmark).

Detection of the immunocomplex (e.g. CD24 and/or CD11b immunocomplex) in leukocytes can be performed using fluorescence activated cell sorting (FACS), enzyme linked immunosorbent assay (ELISA) e.g., sandwich ELISA assay, Western blot and radio-immunoassay (RIA) analyses, immunoprecipitation (IP) or by a molecular weight-based approach.

FACS analysis enables the detection of antigens present on cell membranes such as CD24 and/or CD11b. Briefly, specific antibodies (e.g. CD24 and/or CD11b specific antibodies) are linked to fluorophores and detection is performed by means of a cell sorting machine which reads the wavelength of light emitted from each cell as it passes through a light beam. This method may employ two or more antibodies simultaneously.

The level of CD24 and/or CD11b (or any of the other cell markers described above) can be also determined using ELISA. Briefly, a sample containing e.g. CD24 and/or CD11b antigen is fixed to a surface such as a well of a microtiter plate. An antigen specific antibody (e.g. a CD24 and/or CD11b antibody) coupled to an enzyme is applied and allowed to bind to the antigen. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

For Western blot the proteins are extracted from a cell sample and are subjected to electrophoresis (e.g., SDS-PAGE) and blotting to a membrane (e.g., nitrocellulose or PVDF). The membrane is then interacted with an antibody (e.g. a CD24 and/or CD11b antibody) which can be either directly labeled or further subjected to a secondary labeled antibody. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

In case the concentration of the antigen in the biological sample is low, detection of the antigen (e.g. CD24 and/or CD11b amino acid sequence) can be performed by immunoprecipitation (IP). For immunoprecipitation analysis the antibody (e.g. CD24 and/or CD11b antibody) may directly interact with a sample (e.g., cell lysate) including e.g. CD24 and/or CD11b and the formed complex can be further detected using a secondary antibody conjugated to beads (e.g., if the CD24 and/or CD11b antibody is a mouse monoclonal antibody, the secondary antibody may be an anti-mouse antibody conjugated to e.g., Sepharose beads). The beads can be then precipitated by centrifugation, following which the precipitated proteins (e.g., CD24 and/or CD11b and anti-CD24 and/or anti-CD11b antibodies) can be detached from the beads (e.g., using denaturation at 95° C.) and further subjected to Western blot analysis using the specific antibodies (e.g. CD24 and/or CD11b specific antibodies). Alternatively, the antibody, e.g. anti-CD24 and/or anti-CD11b antibody, and the beads-conjugated secondary antibody may be added to the biological sample containing the antigen (e.g. CD24 and/or CD11b) to thereby form an immunocomplex. Alternatively, for example, since CD24 and/or CD11b is a highly glycosylated protein, it can be also precipitated using a substrate capable of binding glycosylated polypeptides such as Concavalin A (GE Healthcare Bio-Sciences, Uppsala, Sweden) which may be also conjugated to beads, followed by Western blot analysis with e.g. anti-CD24 and/or anti-CD11b antibodies.

The level of CD24 and/or CD11b (or any of the other cell markers described above) can be also determined using radio-immunoassay (RIA). In one version, this method involves precipitation of the desired antigen (e.g. CD24 and/or CD11b) with a specific antibody and radiolabeled antibody binding protein (e.g., protein A labeled with $I^{125}$) immobilized on a precipitable carrier such as agarose beads. The number of counts in the precipitated pellet is proportional to the amount of antigen.

In an alternate version of the RIA, a labeled antigen and an unlabelled antibody binding protein are employed. A sample containing an unknown amount of antigen is added in varying amounts. The decrease in precipitated counts from the labeled antigen is proportional to the amount of antigen in the added sample.

The level of CD24 and/or CD11b (or any of the other cell markers described above) can also be determined using molecular weight-based approach. Since the immunocomplex exhibits a higher molecular weight than its components, methods capable of detecting such a change in the molecular weight can be also employed. For example, the immunocomplex can be detected by a gel retardation assay. Briefly, a non-denaturing acrylamide gel is loaded with samples. A shift in the size (molecular weight) of the protein product as compared with its components is indicative of the presence of an immunocomplex. Such a shift to a higher molecular weight can be viewed using a non-specific protein staining such as silver stain or Commassie blue stain.

It will be appreciated that analyzing an amount of CD24 and/or CD11b (or any of the other cell markers described above) in leukocytes may also be effected on the polynucleotide level. RNA detection methods can be performed using an isolated polynucleotide (e.g., a polynucleotide probe, an oligonucleotide probe/primer) capable of hybridizing to a nucleic acid sequence, e.g. a CD24 and/or CD11b nucleic acid sequence such as the CD24 and/or CD11b transcript or a portion thereof, respectively. Such a polynucleotide can be at any size, such as a short polynucleotide (e.g., of 15-200 bases), an intermediate polynucleotide of 100-2000 bases and a long polynucleotide of more than 2000 bases.

The isolated polynucleotide probe used by the present invention can be any directly or indirectly labeled RNA molecule [e.g., RNA oligonucleotide (e.g., of 17-50 bases), an in vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to the RNA transcript, e.g. CD24 and/or CD11b RNA transcript of the present invention.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The isolated polynucleotide used by the present invention can be labeled either directly or indirectly using a tag or label molecule. Such labels can be, for example, fluorescent molecules (e.g., fluorescein or Texas Red), radioactive molecule (e.g., $^{32}P$-$\gamma$-ATP or $^{32}P$-$\alpha$-ATP) and chromogenic substrates [e.g., Fast Red, BCIP/INT, available from (AB-CAM, Cambridge, Mass.)]. Direct labeling can be achieved by covalently conjugating a label molecule to the polynucleotide (e.g., using solid-phase synthesis) or by incorporation via polymerization (e.g., using an in vitro transcription reaction or random-primed labeling). Indirect labeling can be achieved by covalently conjugating or incorporating to the polynucleotide a non-labeled tag molecule (e.g., Digoxigenin or biotin) and subsequently subjecting the polynucleotide to a labeled molecule (e.g., anti-Digoxigenin antibody or streptavidin) capable of specifically recognizing the non-labeled tag.

The above-described polynucleotides can be employed in a variety of RNA detection methods such as Northern blot analysis, reverse-transcribed PCR (RT-PCR) [e.g., a semi-quantitative RT-PCR, quantitative RT-PCR using e.g., the Light Cycler™ (Roche)], RNA in situ hybridization (RNA-ISH), in situ RT-PCR stain [e.g., as described in Nuovo G J, et al. 1993, Intracellular localization of polymerase chain reaction (PCR)-amplified hepatitis C cDNA. Am J Surg Pathol. 17: 683-90, and Komminoth P, et al. 1994, Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract., 190: 1017-25] and oligonucleotide microarray analysis [e.g., using the Affymetrix microarray (Affymetrix®, Santa Clara, Calif.)].

As mentioned, a level of CD24 on small leukocytes and not on large leukocytes above a predetermined threshold is indicative of the cancer or the pre-malignant lesion The "predetermined threshold" may be experimentally determined by comparing normal leukocytes samples (e.g., samples obtained from healthy subjects) to leukocytes samples derived from subjects known to have cancer or a premalignant lesion (e.g. colorectal cancer, pancreatic cancer, early carcinoma, sarcoma, multiple myeloma etc.). Preferably, a statistically significant number of samples are analyzed.

According to one embodiment, analyzing the level of CD24 on small leukocytes and not on large leukocytes may be carried out by calculating the total expression of CD24$^+$ leukocytes in a sample (i.e. on all small and large leukocytes), by calculating the dual expression of CD24$^+$ and CD11b$^+$ leukocytes in a sample (i.e. demonstrating large leukocytes), and subtracting the number of CD24$^+$ CD11b$^+$ leukocytes from the total number of CD24$^+$ leukocytes.

According to one embodiment, analyzing the level of CD24 on small leukocytes and not on large leukocytes may be carried out by calculating the number of cells expressing CD24 and not expressing CD11b.

According to one embodiment, analyzing the level of CD24 on small leukocytes and not on large leukocytes may be carried out by calculating the number of T cells, e.g. cells expressing CD24, CD3, CD4 and/or CD8.

According to one embodiment, analyzing the level of CD24 on small leukocytes and not on large leukocytes may be carried out by calculating the number of B cells, e.g. cells expressing CD24, CD19 and/or CD20.

According to one embodiment, analyzing the level of CD24 on small leukocytes and not on large leukocytes may be carried out by calculating the number of monocytes, e.g. cells expressing CD24, CD33, CD14 and/or CD16.

According to one embodiment, analyzing the level of CD24 on small leukocytes and not on large leukocytes may be carried out by calculating the number of T cells, e.g. cells expressing CD24, CD3, CD4 and/or CD8, and B cells, e.g. cells expressing CD24, CD19 and/or CD20.

According to one embodiment, analyzing the level of CD24 on small leukocytes and not on large leukocytes may be carried out by calculating the number of T cells, e.g. cells expressing CD24, CD3, CD4 and/or CD8, and monocytes, e.g. cells expressing CD24, CD33, CD14 and/or CD16.

According to one embodiment, analyzing the level of CD24 on small leukocytes and not on large leukocytes may be carried out by calculating the number of B cells, e.g. cells expressing CD24, CD19 and/or CD20, and monocytes, e.g. cells expressing CD24, CD33, CD14 and/or CD16.

According to one embodiment, analyzing the level of CD24 on small leukocytes and not on large leukocytes may be carried out by calculating the number of T cells, e.g. cells expressing CD24, CD3, CD4 and/or CD8, B cells, e.g. cells expressing CD24, CD19 and/or CD20, and monocytes, e.g. cells expressing CD24, CD33, CD14 and/or CD16.

According to one embodiment, a limited number of cellular markers e.g., 2-10, 2-9, 2-8, 2-7, 2-6, 2-5, 2-4 or 2-3 cellular markers are analyzed.

According to a specific embodiment only 2 cellular markers are analyzed (e.g. CD24 and CD11b).

According to a specific embodiment 3 cellular markers are analyzed (e.g. CD24, CD3 and CD11b; CD24, CD4 and CD11b; CD24, CD8 and CD11b; CD24, CD3 and CD4; CD24, CD3 and CD8; CD24, CD19 and/or CD11b; CD24, CD20 and/or CD11b; CD24, CD14 and/or CD11b; CD24, CD16 and/or CD11b; CD24, CD33 and/or CD11b; CD24, CD14 and/or CD16; CD24, CD14 and/or CD33; CD24, CD16 and/or CD33).

According to a specific embodiment 4 cellular markers are analyzed (e.g. CD24, CD3, CD4 and CD11b; CD24, CD3, CD8 and CD11b; CD24, CD19, CD20 and CD11b; CD24, CD33, CD14 and CD11b; CD24, CD33, CD16 and CD11b; CD24, CD14, CD16 and CD11b).

It will be appreciated that the presence of the cancer or the pre-malignant lesion can be further validated using additional assays. For example, in case the level of CD24 detected in small leukocytes of a subject is above a predetermined threshold, additional assays such as tissue biopsy, histology, CT scan (Computed Tomography), MRI (Magnetic Resonance Imaging), X-ray, ultrasound, mammography, endoscopy, and/or colonoscopy may be performed.

It will be appreciated that the present teachings may also be used to determine treatment efficacy. Thus determining CD24 expression on small leukocytes may be effected following and optionally prior to anti-cancer therapy, whereby a reduction of CD24 expression on small leukocytes and not on large leukocytes is indicative of treatment efficacy.

According to another aspect of the present invention, there is provided a method of treating a cancer or a pre-malignant lesion in a subject in need thereof, the method comprising administering a therapeutic agent for the treatment of the cancer or the pre-malignant lesion to the diagnosed subject.

According to another aspect of the present invention, there is provided a therapeutic agent for use in treating cancer or a pre-malignant lesion in a subject in need thereof, wherein the subject has been diagnosed with a cancer or a premalignant lesion.

Exemplary therapeutic agents for the treatment of cancer include, but are not limited to, chemotherapy, radiotherapy, phototherapy and photodynamic therapy, surgery, nutritional therapy (e.g. dietary supplement), ablative therapy, combined radiotherapy and chemotherapy, brachiotherapy, proton beam therapy, immunotherapy (e.g. cancer vaccine or antibody immunotherapy), cellular therapy, photon beam radiosurgical therapy.

Non-limiting examples of chemotherapeutic agents include, but are not limited to, platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

According to another aspect of the invention, the agent for determining a level of CD24 expression and the agent for determining a level of CD11b expression may be packaged in a kit and labeled for the use of diagnosing a cancer or a pre-malignant lesion.

According to one embodiment, when the agent is a polypeptide agent (e.g. anti-CD24 and/or anti-CD11b antibody), the kit may further include reagents for FACS analysis. Additionally or alternatively, the kit may comprise reagents for Western Blot analysis and at least one precast gel for performing the Western Blot.

According to one embodiment, when the agent is an oligonucleotide agent (e.g. polynucleotide probe), the kit may further include a DNA polymerase enzyme, such as a thermostable DNA polymerase, a reverse transcriptase enzyme, a mixture of dNTPs, a concentrated polymerase chain reaction buffer and a concentrated reverse transcription buffer. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. The kit may also comprise at least one precast gel for performing RT-PCR. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents.

The kit of the invention preferably includes a notice associated therewith in a form prescribed by a governmental agency regulating the manufacture, use or sale of diagnostic kits. Detailed instructions for use, storage and troubleshooting may also be provided with the kit.

According to another aspect of the invention, there is provided a composition comprising at least about 50%, 55%, 60%, 65%, 70%, 75%, 80%, 85%, 90%, 95%, 99% or more small leukocytes and a CD24 targeting antibody.

According to a specific embodiment of the invention, there is provided a composition comprising at least 70% small leukocytes and a CD24 targeting antibody.

According to a specific embodiment of the invention, there is provided a composition comprising at least 80% small leukocytes and a CD24 targeting antibody.

According to a specific embodiment of the invention, there is provided a composition comprising at least 90% small leukocytes and a CD24 targeting antibody.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Isolation of Peripheral Blood Leukocytes

Blood was collected into 9 ml collection tubes (Vacuette®, Greiner bio-one). All samples were collected and processed identically. Peripheral blood leukocytes (PBLs) were isolated from blood samples by collecting buffy coats obtained after centrifugation for 3 minutes at 3000 rpm and discarding the plasma supernatant. Residual erythrocytes were lysed by brief incubation in erythrocyte lysis buffer (ELB) containing 155 mM $NH_4Cl$, 0.1 mM EDTA, and 10 mM $KHCO_3$. The resulting pellet was washed in PBS and cells were fixed with 2% formaldehyde. Cells were than counted and subjected to flow cytometry assay.

Subjects

PBLs from patients and age and gender matched healthy individuals were separated from freshly drawn blood. All samples were collected and processed identically. The samples were obtained from volunteers at Tel Aviv Sourasky Medical Center and Rabin Medical Center. Eligible subjects completed a detailed medical questionnaire including cancer diagnoses, demographic data, and other epidemiologic information.

Flow Cytometry Assay

For each sample, 20,000 leukocytes were analyzed. Single-cell suspensions of human leukocytes were stained using the following antibodies: anti-CD11b-PerCp-Cy5.5 (M1/70) (Tombo Bioscience) and humanized anti-CD24-FITC (produced by the preset inventors). The percentage of $CD24^+CD11b^-$ cells was determined by subtracting the percentage of CD24 and CD11b-positive cells (dual stain) from CD24-positive cells (single stain).

Blood was collected into 9 ml collection tubes (Vacuette®, Greiner bio-one). All samples were collected and processed identically. PBLs were isolated from blood samples by collecting buffy coats obtained after centrifugation for 3 minutes at 3000 rpm and discarding the plasma supernatant. Residual erythrocytes were lysed by brief incubation in erythrocyte lysis buffer. The resulting pellet was washed in PBS and fixed with 2% formaldehyde. Cells were counted and subjected to flow cytometry assay.

Cellular CD24 and CD11b was evaluated by flow cytometry. Approximately $1 \times 10^6$ cells were used in each experiment. After trypsinization, the cells were washed in fluorescence-activated cell sorting buffer and fixed with 2% formaldehyde for 15 minutes at room temperature (RT). After washing with FACS buffer, 100 µl of the different labeled-antibodies were added for 30 minutes at RT. After washing ×3 with FACS buffer, detection of bound antibodies was performed on a CyFlow® Cube 6 (Sysmex Europe GmbH) and results were analysed with the FCS express program.

Example 1

Diagnosing Cancer Using Dual Expression of CD24 and CD11b on Leukocytes

Using gene expression array, some inventors of the present invention have previously shown that CD24 is differentially expressed in normal and transformed enterocytes, reverting back to normal levels following short and long exposure to COX-2 inhibition [Sagiv, E. et al., *Gastroenterology* (2006) 31(2):630-9; Sagiv, E. et al., *Digestion* (2011) 84(3): 169-84; Sagiv, E. et al., *Clin Cancer Res* (2007) 3(22 Pt 1):6807-15]. CD24 expression was detected in 90.7% of colorectal adenomas and 86.3% of CRCs compared to weak expression in 16% of adjacent normal epithelium. Similar results were obtained for other GI cancers [Sagiv, E. et al., *Gastroenterology* (2006), supra].

Peripheral blood leukocytes (PBL) are the body sensors. They travel throughout the body, entering and exiting tissues with inflammation and neoplasia. Hence, they can serve as messengers. Some inventors of the present invention have previously shown that expression level of CD24 in PBLs may be used for early detection of colorectal adenomas and CRC [Kraus et al., *Dis Markers* (2009), supra]. According to Kraus et al., western blotting (WB) analysis for CD24 level on PBL lysates had good sensitivity and specificity for detecting colorectal adenomas as compare to healthy subjects with normal colonoscopy. Therefore, it was concluded from Kraus et al. that CD24 alone may be a useful clinical tool for screening asymptomatic individuals for colorectal cancer. Although western blotting is a common procedure for diagnostic labs, it has several disadvantages: it is a qualitative tool, it is labor intensive, and it is expensive. Accordingly, the present work concentrated on developing a better screening assay for cancers and pre-cancers using CD24 marker expression and utilizing flow cytometry.

For flow cytometry analysis, PBLs from patients and healthy individuals were separated from freshly drawn blood. Single-cell suspensions were stained using: anti-CD11b-PerCp-Cy5.5 and anti-CD24-FITC. The present inventors uncovered that in healthy subjects CD24 is expressed on large cell types (such as neutrophils, granulocytes). Since CD11b is expressed on the surface of these large cells, staining the purified PBLs with CD24 and CD11b markers (single and double stain) allowed to distinguish between different cell populations e.g. between cells of normal and cancer (e.g. CRC, PC and MM) patients. The percentage of $CD24^+CD11b^-$ cells was determined by subtracting the percentage of CD24 and CD11b-positive cells (dual stain) from CD24-positive cells (single stain).

Data was analyzed following the creation of a hierarchical population tree in the software at the beginning of the screen. This template was used in all subsequent analyses. The template file included compensation adjustment, which was uniformly applied to all the data collected in order to minimize fluorescence overlap between detection channels. The normal control population included healthy individuals who underwent a thorough and extensive examination at the Integrated Cancer Prevention Center at Tel-Aviv Medical Center as previously discussed [Sella T. et al., *Eur J Intern Med* (2013) 24(3): 245-9]. Cancer was verified by histology in all patients.

Figure 1A:
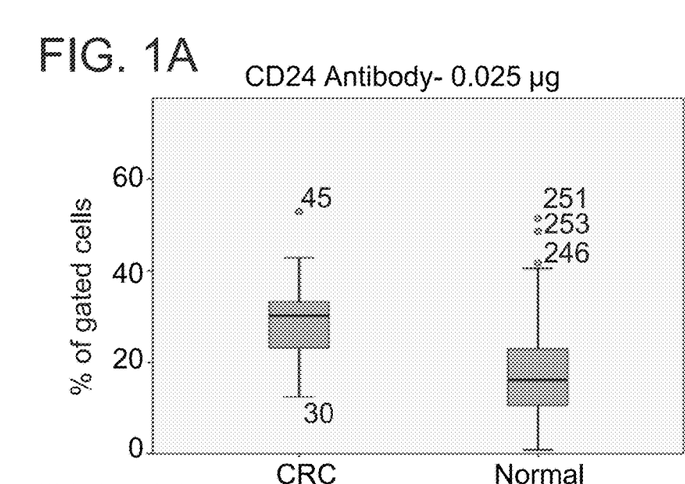
FIGS. 1A-E are graphs illustrating the distribution of patients with colorectal cancer (CRC, FIGS. 1A-1B), pancreatic cancer (PC, FIGS. 1C-1D) and multiple myeloma (MM, FIG. 1E) compared to Normal (healthy) subjects. Box plots represent the percentage of cells expressing CD24 and negative for CD11b (i.e. CD24$^+$CD11b$^-$ cells) as determined by flow cytometry. The two panels for each type of cancer, i.e. for CRC and PC, represent two concentrations of CD24 antibody that has been used. Black lines across each graph represent median values.
Figure 1B:
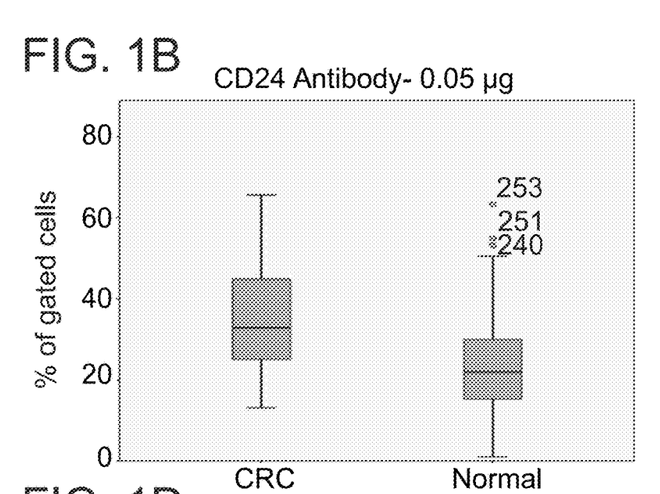
Figure 1C:
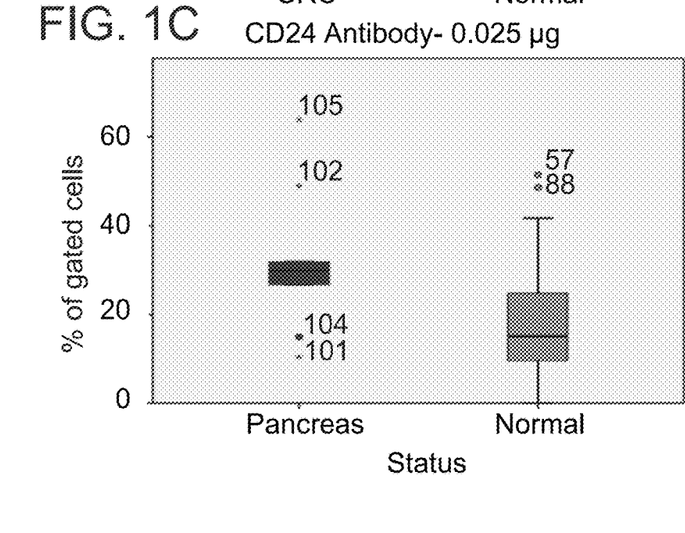
Figure 1D:
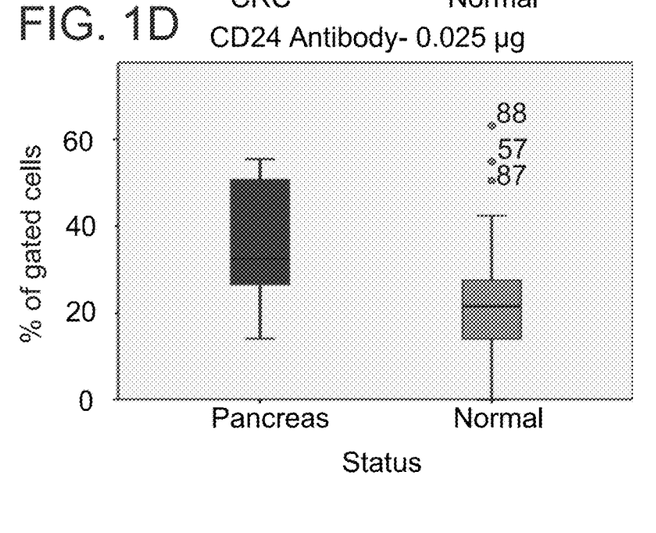
Figure 1E:
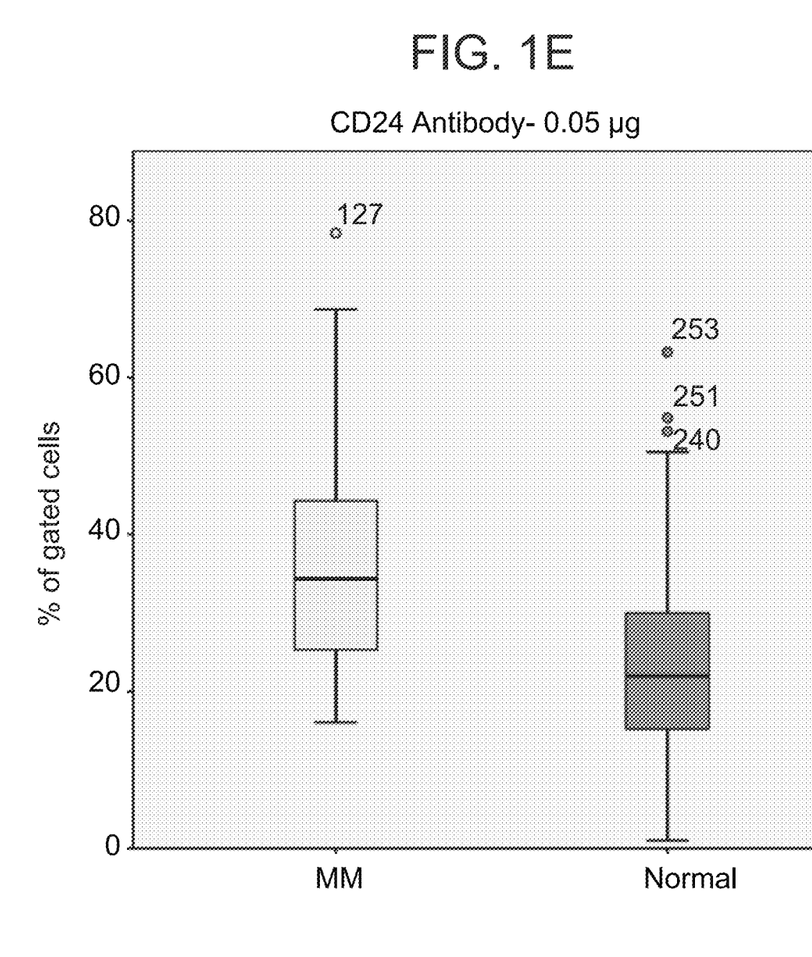
Figure 1F:
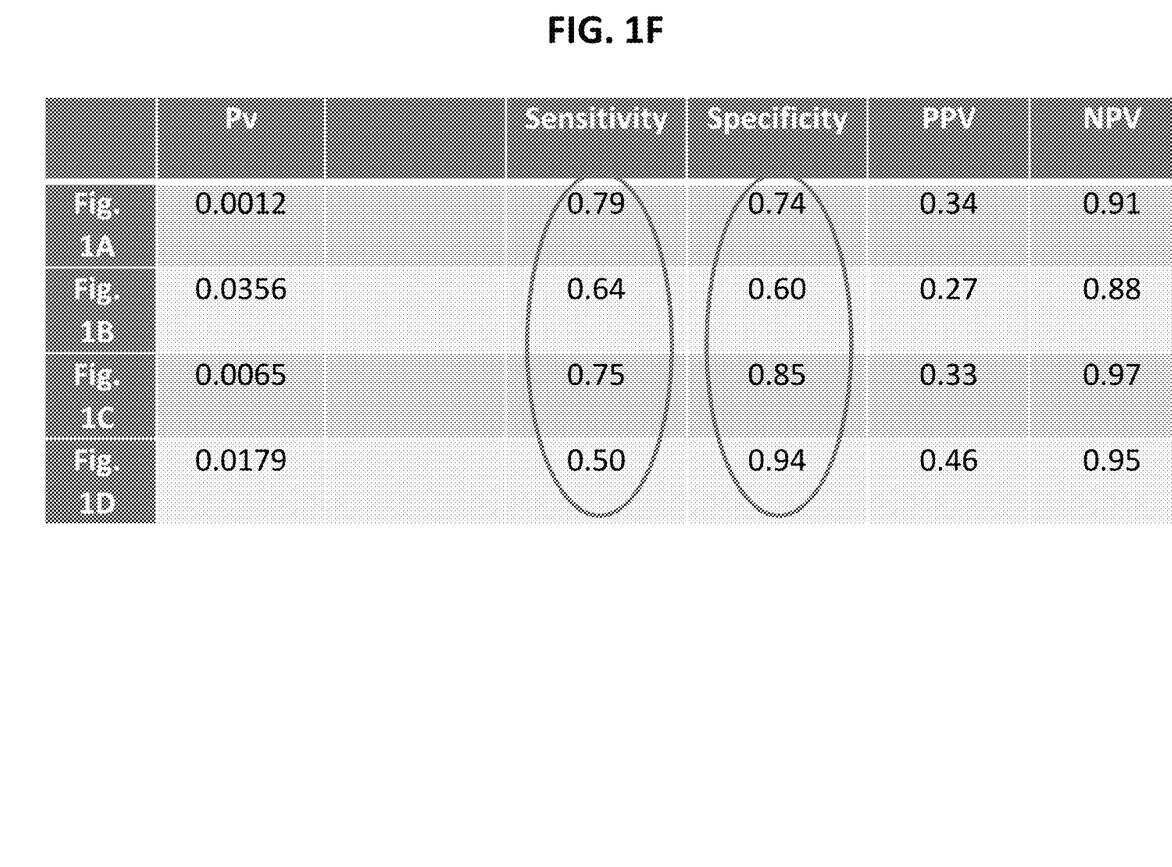
FIG. 1F is a table summarizing the P value, sensitivity, specificity, positive predictive value and negative predictive value of the subjects tested in FIGS. 1A-1D, above.
Figure 2A:
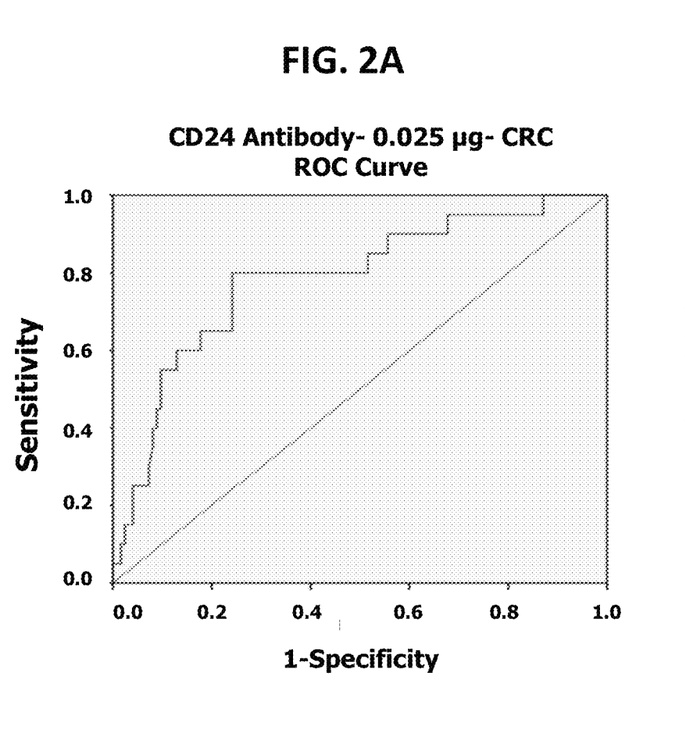
FIG. 2A shows Normal vs. CRC (0.025 µg Ab)
Figure 2B:
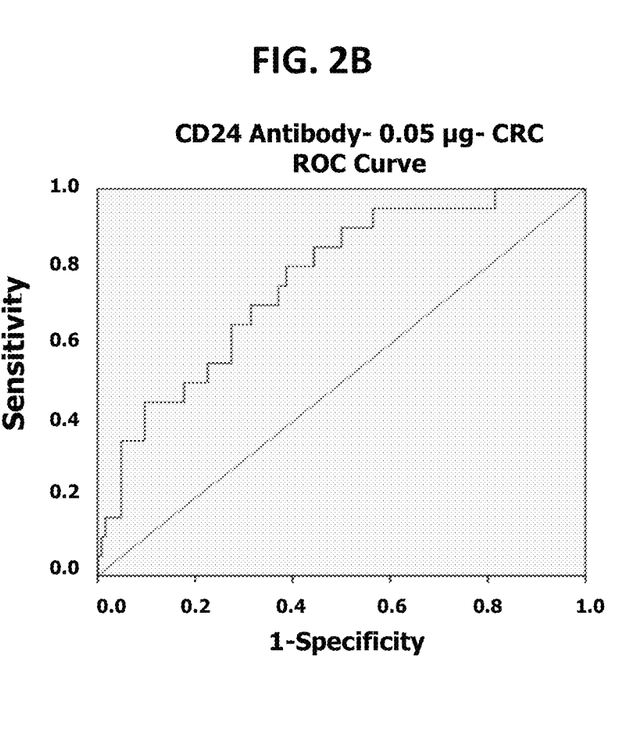
FIG. 2B shows Normal vs. CRC (0.05 µg Ab)
Figure 2C:
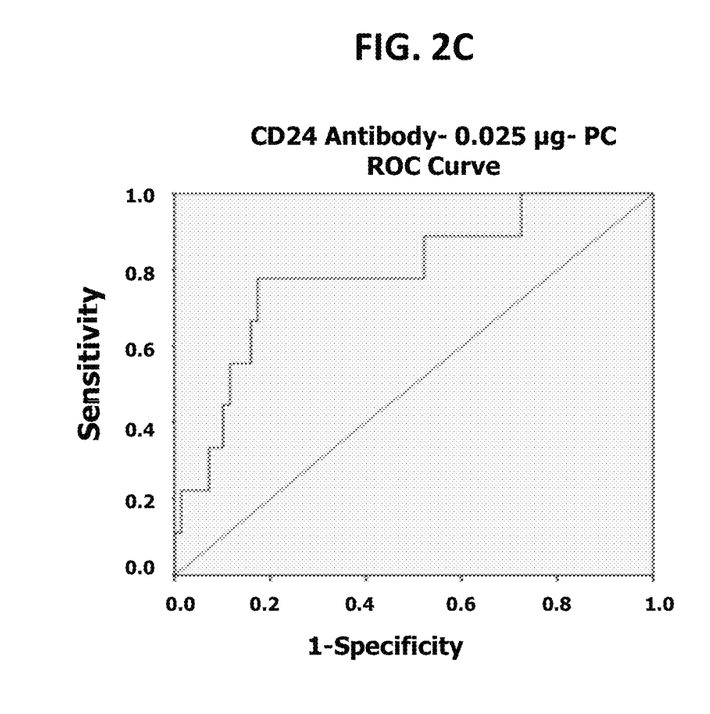
FIG. 2C shows Normal vs. PC (0.025 µg Ab)
Figure 2D:
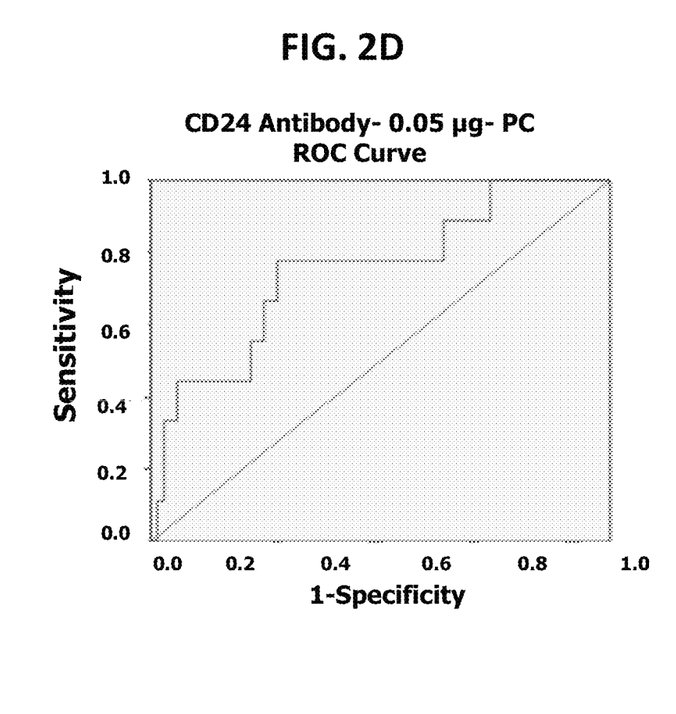
FIG. 2D shows Normal vs. PC (0.05 µg Ab).
Figure 3A:
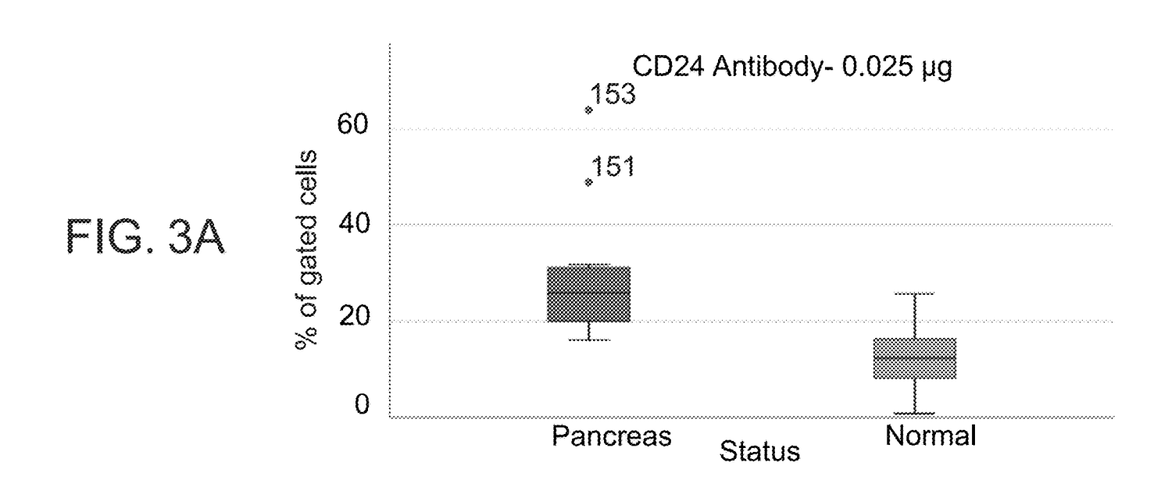
FIGS. 3A-B are graphs illustrating the distribution of an additional study including patients with pancreatic cancer compared to Normal (healthy) subjects. Two concentration of the anti-CD24 mAb were used. Box plots represent the percentage of cells expressing CD24 and negative for CD11b (i.e. CD24$^+$CD11b$^-$ cells) as determined by flow cytometry.
Figure 3B:
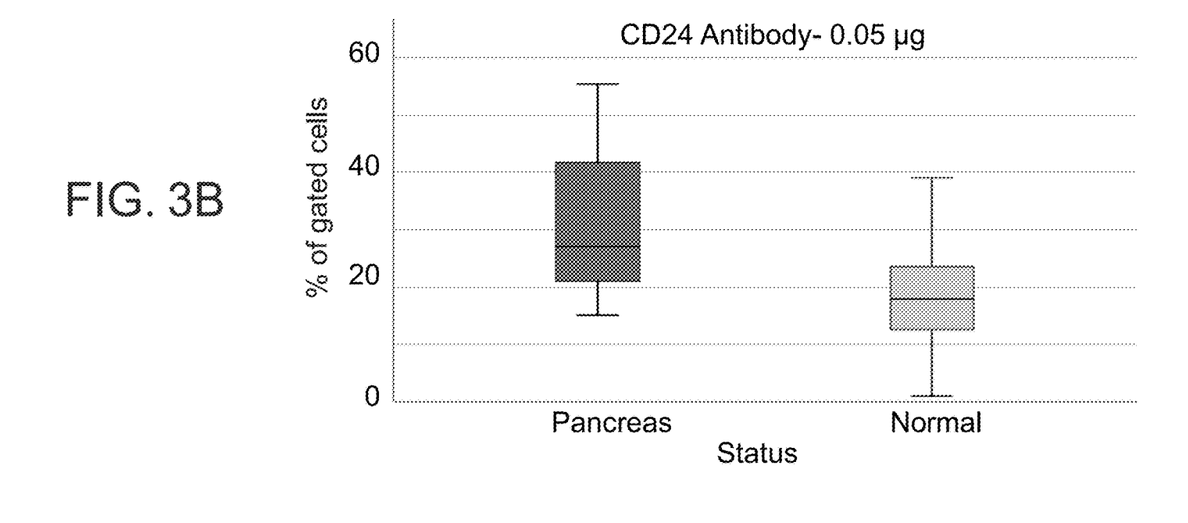

The CD24 results were dichotomized based on whether they were above or below the cut-off level (26-30% CD24 expression). The sensitivity, specificity and positive and negative predictive values were also determined. Discrimination of the CD24 test between patients with levels above and below the threshold was quantified by the area under the ROC curve (AUC) and was reported with 95% confidence intervals (CI). The results indicated the ability to detect cancer, and to distinguish healthy individuals from colorectal cancer (CRC) ($P<0.013$, see FIGS. 1A-B), pancreatic cancer (PC) ($P<0.018$, see FIGS. 1C-D and FIGS. 3A-B), biliary tract ($P<6.45E-12$, data not shown), sarcoma ($P<0.036$, data not shown) and multiple myeloma ($P<0.4E-08$, see FIG. 1E). The sensitivity and specificity of CD24 for distinguishing CRC from normal subjects was 79.2% and 74.7%, respectively, with AUC of 0.786 (see FIGS. 2A-B) and for detecting PC were 75.0% and 85%, respectively, with an AUC of 0.791 (see FIGS. 2C-D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method treating a cancer or a pre-malignant lesion in a subject in need thereof, the method comprising:
    (a) diagnosing a cancer or a pre-malignant lesion in the subject by determining a level of expression of CD24 and CD11b on leukocytes comprised in a biological sample of the subject so as to determine a number of leukocytes having a $CD24^+CD11b^-$ signature and not having a $CD24^+CD11b^+$ signature, and wherein said number of leukocytes having a $CD24^+CD11b^-$ signature above a predetermined threshold is indicative of said cancer or said pre-malignant lesion; and
    (b) administering a therapeutic agent for the treatment of the cancer or the pre-malignant lesion to the diagnosed subject,
    thereby treating cancer or a pre-malignant lesion in the subject in need thereof.

2. The method of claim 1, further comprising corroborating the diagnosis using a diagnostic assay selected from a biopsy, a histology, a CT scan (Computed Tomography) and an MRI (Magnetic Resonance Imaging).

3. The method of claim 1, wherein said sample is selected from the group consisting of a blood sample, a serum sample, a stool sample, a urine sample and a saliva sample.

4. The method of claim 1, wherein said pre-malignant lesion is an adenoma.

5. The method of claim 1, wherein said pre-malignant lesion is associated with a solid tumor.

6. The method of claim 1, wherein said cancer is a solid tumor.

7. The method of claim 5, wherein said solid tumor is a gastrointestinal tract cancer.

8. The method of claim 5, wherein said solid tumor is selected from the group consisting of colorectal cancer, cancer of the small intestine, stomach cancer, pancreatic cancer, liver cancer, gall-bladder cancer, biliary tract cancer, esophageal cancer, oral cavity cancer, prostate cancer, testicular cancer, lung cancer, breast cancer, urinary tract cancer, kidney cancer, bladder cancer, uterine cancer, cervical cancer, ovarian cancer, fallopian tube cancer, sarcoma, melanoma, squamous cell carcinoma, brain cancer and glioma.

9. The method of claim 1, wherein said cancer is a hematopoietic malignancy.

10. The method of claim 9, wherein said hematopoietic malignancy is selected from the group consisting of a lymphoma, a leukemia and a multiple myeloma.

11. A method of monitoring efficacy of cancer therapy, the method comprising measuring expression of CD24 and CD11b on leukocytes comprised in a biological sample of a subject having been treated with a cancer therapy so as to determine a number of leukocytes having a $CD24^+CD11b^-$ signature and not having a $CD24^+CD11b^+$ signature, and wherein a decrease in said number of leukocytes having a $CD24^+CD11b^-$ signature beyond a predetermined threshold following the cancer therapy is indicative of reduction of said cancer, thereby monitoring efficacy of the cancer therapy.

* * * * *